United States Patent [19]
Murakami et al.

[11] Patent Number: 5,945,512
[45] Date of Patent: Aug. 31, 1999

[54] PRORENIN ANTIBODY AND RENIN-ACTIVE SUBSTANCE CONTAINING THE SAME

[75] Inventors: Kazuo Murakami, Tsukuba; Yukio Nakamura; Fumiaki Suzuki, both of Gifu; Yuichi Ishida, 8-205, West Heights, 1947, Oaza Higashiowa, Washimiya-machi, Kitakatsushika-gun, Saitama; Yasuhiko Hatano, Tokorozawa, all of Japan

[73] Assignees: Tokiwa Chemical Industries Co., Ltd.; Yuichi Ishida, both of Japan

[21] Appl. No.: 09/054,260

[22] Filed: Apr. 3, 1998

[30] Foreign Application Priority Data

Apr. 7, 1997 [JP] Japan ......................................... 9-88538

[51] Int. Cl.⁶ .......................... C07K 16/00; G01N 33/53
[52] U.S. Cl. .................................. 530/387.1; 530/387.9; 435/7.1
[58] Field of Search .......................... 435/7.1; 530/387.1, 530/387.9, 388.26

[56] References Cited

FOREIGN PATENT DOCUMENTS 3-87200    4/1991    Japan .
8-285852  11/1996   Japan .

OTHER PUBLICATIONS

J. Luetscher et al. *New England J. Med.*, 312(22), 1412–1417 (May 30, 1985).

K. Naruse et al., *Tokyo Women's Medical College*, 60, 342–350 (1990).

M. Schalekamp, *Clin. Investig.*, 71, S3–S6 (1993).

F. Derkx et al., *Clin. Chem.*, 42(7), 1051–1063 (1996).

M. Schumacher et al., *J. Clin. Endocrin. and Metab.*, 75(2), 617–623 (1992).

F. Suzuki et al., *Clin. and Exper. Hyper.–Theory and Practice*, A12(1), 83–95 (1990).

K. Kataoka et al., *Biomed. Res.*, 16(6), 363–370 (1995).

R. Day et al., *J. Hypertension*, 4(3), 375–381 (1986).

M. Price–Jones et al., *Clin. and Exper. Hypertension*, 15(4), 619–640 (1993).

*Primary Examiner*—James C. Housel
*Assistant Examiner*—S. Devi
*Attorney, Agent, or Firm*—Wederoth, Lind & Ponack, L.L.P.

[57] ABSTRACT

Provided by the present invention are a human prorenin profragment N-terminated peptide antibody capable of specifically recognizing a peptide containing at least 15 amino acid residues from the first leucine residue to the 15th arginine residue in the N-terminated peptide of the human prorenin profragment and a complex of the same with human prorenin. The antibody can be used as a prorenin assay reagent. The human prorenin profragment N-terminated peptide antibody is useful as a reagent for the assay of human prorenin in blood.

3 Claims, 6 Drawing Sheets

PRORENIN ANTIBODY AND RENIN-ACTIVE SUBSTANCE CONTAINING THE SAME

BACKGROUND OF THE INVENTION

The present invention relates to a novel N-terminated peptide antibody of the profragment of human prorenin, referred to as "pf" hereinafter, capable of forming an immune complex by combining with human prorenin, a renin-active substance formed when the antibody is combined with human prorenin and an assay reagent for prorenin by using the same.

Prorenin is a substance having no enzyme activity, which is produced mainly in the kidney as a precursor of the renin of the completely matured type or, namely, as the renin of the completely matured type combined with a profragment consisting of 43 amino acid residues. It is known that, when diabetes causes vascular disorders, the concentration of human prorenin in blood is increased depending on the seriousness of the disease while the concentration is decreased along with alleviation of the disease. It is proposed accordingly to take the concentration of human prorenin in blood as a marker of the diabetic vascular disorder (see The New England Journal of Medicine, volume 312, 1985, pages 1412–1417, Memoirs of Tokyo Women's Medical College, volume 60, 1990, pages 342–350, and Clinical Investigator, volume 71, 1993, pages 3–6).

In connection therewith, several proposals have been made heretofore for the assay of the prorenin concentration in human plasma. A problem in these prior art methods is that, because human plasma contains both of the renin of the completely matured type as an enzymatic protein and the enzymatically inactive human prorenin as a precursor of the renin of the completely matured type, an indirect method must be undertaken in which the human prorenin in plasma is first partially activated with an acid at a low temperature and then converted into the renin of the completely matured type by using trypsin followed by the determination of the overall amount of renin by an enzymological method as the overall amount of renin activity or by an immunological method as the overall amount of active renin and the amount of the human prorenin is calculated as a difference obtained by subtracting the separately obtained value of the renin activity by an enzymological method or the amount of active renin by an immunological method from the above obtained overall renin activity or overall amount of active renin.

The "renin of the completely matured type" here implied is a structural body derived from prorenin after separation of the profragment part therefrom by a processing enzyme and can exhibit the renin activity since the enzymatically active part is open. The renin activity above mentioned is the enzymatic activity as an inherent function of the renin of the completely matured type which is an enzyme protein or, namely, the activity to produce angiotensin (Ang I) by selectively acting on the renin substrate (angiotensinogen).

A discovery was recently made to convert inactive human prorenin into an open-type structure by utilizing the effect of bonding thereof with a low-molecular renin inhibitor and, as a result of this discovery, a possibility has been established of an immunological method for the assay of the overall renin activity by utilizing a monoclonal antibody capable of specifically recognizing the proximity of the renin active part and a monoclonal antibody capable of recognizing both of the human prorenin and the renin of the completely matured type along with development of a method in which the amount of active renin is determined without addition of a renin inhibitor to calculate the amount of human renin from the difference between the overall active renin and the active renin determined as above (see Clinical Chemistry, volume 42, 1996, pages 1051–1063). As compared with the prior art method for the trypsin-activated enzymological method or the trypsin activation method for the assay of renin activity, this method, though advantageous in respect of the possibility of suppressing transient decomposition of the human prorenin and renin of the completely matured type by trypsin as well as in the good correlation with the trypsin activation method, has a defect that the renin activity obtained thereby is positively biased as compared with the true renin activity for diabetic cases where an increase is noted in the prorenin titer in blood. Moreover, this method is troublesome because the assay must be conducted each time for the renin activity and for the overall renin activity.

Besides, an immunological method of assay is known which is a direct method by utilizing a monoclonal antibody capable of recognizing the C-terminal of the pf in the human prorenin or, namely, the 29th to 43rd amino acid residues as an antigen and a renin monoclonal antibody capable of recognizing both of the human prorenin and renin of the completely matured type (see Journal of Clinical Endocrinology and Metabolism, volume 75, 1992, pages 617–623).

This method is advantageous because the method has, in addition to the very good correlation with the trypsin activation method, a sensitivity so high that the method can be used even for the assay of the prorenin titer in blood taken from a healthy person. On the other hand, the method has defects in that, as a trend, the value obtained by the assay is negatively biased to be as low as about 80% as compared with the value obtained by the trypsin activation method, this trend being particularly remarkable for a patient of a disease giving an increased human prorenin titer, along with the indefiniteness of the part where the renin monoclonal antibody is recognized.

SUMMARY OF THE INVENTION

The present invention accordingly has a primary object to provide, by overcoming the defects of the trypsin activation method, an indirect method for the assay of human prorenin by means of the assay of the activated overall renin activity utilizing a renin inhibitor and a direct immunological method of assay utilizing an antibody capable of recognizing the C-terminal of pf of the human prorenin as an antigen in the prior art, a reagent for the assay of prorenin capable of accurately and conveniently detecting occurrence of a diabetic vascular disorder.

Thus, the present invention provides an N-terminated peptide antibody of a human prorenin profragment capable of specifically recognizing, as an antigen, a peptide including the amino acid residues from the leucine residue at the first site to the arginine residue at the fifteenth site in the N-terminated peptide of the human prorenin profragment.

Further, the invention provides a novel renin-active substance which is a complex of the human prorenin with the above mentioned N-terminated peptide of the human prorenin profragment. This N-terminated peptide antibody of the human prorenin profragment can be used as the effective ingredient in an assay reagent for prorenin.

DETAILED DESCRIPTION OF THE PREFERRED EMBODIMENTS

Figure 1:
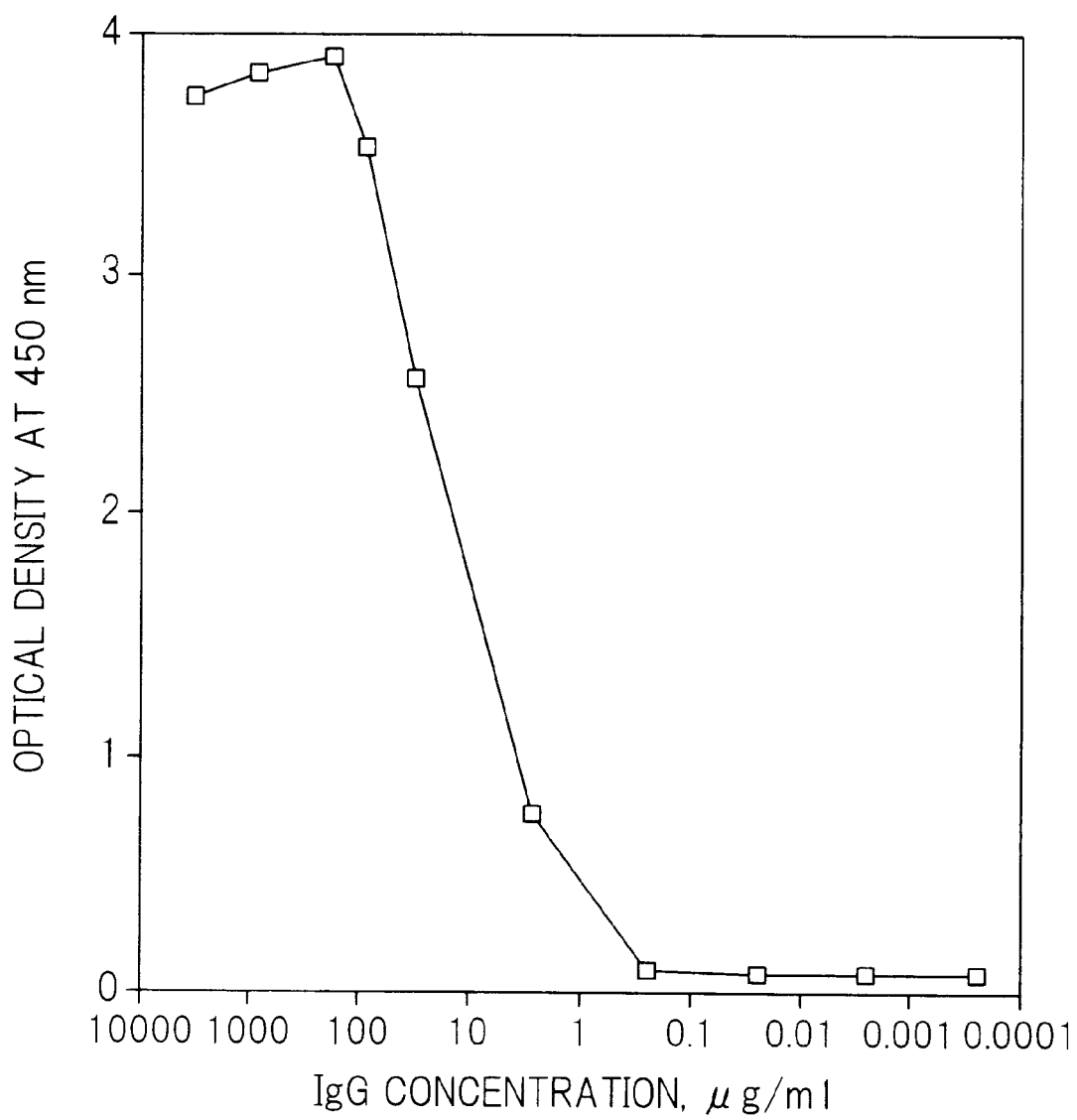
FIG. 1 is a graph showing the relationship between the IgG concentration and amount of human prorenin when human prorenin is reacted with the IgG of the N-terminated peptide antibody of pf.

The inventors previously developed a reagent for the assay of human prorenin by utilizing an antibody capable of specifically recognizing the pf part of human prorenin consisting of 43 amino acid residues (see Japanese Patent Kokai 8-285852). As a result of the further continued investigations, they arrived at a success to obtain a high-affinity antibody capable of specifically recognizing the peptide consisting of 1 to 15 amino acid residues at the pf N-terminal of human prorenin as an antigen and also discovered that a renin active substance was formed when this pf N-terminated antibody was combined with human prorenin to give a possibility of accurately determining the prorenin titer in blood by applying the immunological method for the assay of the Ang I competitive enzyme (see Clinical and Experimental Hypertension—Theory and Practice, volume A12, 1990, pages 83–95) thereto leading to completion of the present invention described above on the base of this discovery.

The pf N-terminated peptide antibody of human prorenin according to the present invention can be prepared, for example, in the following manner.

In the first place, a peptide, which consists of the amino acid residues of Leu-Pro-Thr-Asp-Thr-Thr-Thr-Phe-Lys-Arg-Ile-Phe-Leu-Lys-Arg, corresponding to the pf N-terminated peptide of human prorenin is synthesized by the method of solid phase peptide synthesis and the thus synthesized peptide is combined with a carrier protein such as bovine serum albumin, ovalbumin and keyhole lympet hemocyanin by using a crosslinking agent such as a maleimide compound to give an immunoantigen.

In the next place, each of the immunoantigens is thoroughly admixed with the Freund complete adjuvant and a matured rabbit of about 2.5 kg body weight is immunized by administering the same. This immunizing treatment is repeated once in every two weeks and, after the fifth treatment, a small volume of blood is taken from the vein in the periphery of an earlobe which is subjected to the assay of the antibody titer. When this antibody titer has been sufficiently increased, the rabbit is subjected to whole blood gathering and an antiserum is obtained from the blood. The thus obtained antiserum is subjected to a DEAE Sepharose chromatography to give the pf N-terminated peptide antibody IgG.

Instead of obtaining the polyclonal antibody by immunizing a rabbit with the immunoantigen, alternatively, the monoclonal antibody can be prepared by immunizing mice with the immunoantigen according to a heretofore known method.

The amount of protein was calculated for the pf N-terminated peptide antibody IgG from the optical density at a wavelength of 280 nm by assuming a molecular weight of 150,000 of the IgG to find a titer of 2.6 mg/ml. This pf N-terminated peptide antibody is an antibody exhibiting strong affinity to the human prorenin and acting specifically on the pf N-terminal.

A substance exhibiting an enzymatic activity or, namely, renin activity is obtained by combining this pf N-terminated peptide antibody with the human prorenin. The preparation procedure of this renin-active substance is as follows.

Thus, a human prorenin solution is admixed with the pf N-terminated peptide antibody diluted with a physiological saline solution containing bovine serum and the mixture is kept at a temperature of 4° C. for 16 to 24 hours. Thereafter, the reaction mixture is admixed with a solution of sheep angiotensinogen as a substrate for human prorenin and incubated at 37° C. for 15 minutes to effect further reaction followed by termination of the reaction under chilling in an ice bath.

The renin-active substance obtained in this way is subjected to the measurement of the Ang I-producing activity by making comparison with the human prorenin activated with trypsin to find that the renin activity of the pf N-terminated peptide antibody is varied corresponding to the degree of dilution.

FIG. 1 of the accompanying drawing is a graph, taking the human prorenin of pf N-terminated peptide antibody according to the present invention as an example, showing the relationship between the concentration of IgG in the reaction of the antibody with human prorenin and the optical density of the reaction mixture at a wavelength of 450 nm. This graph is suggestive of the high affinity of the human prorenin pf N-terminated peptide antibody according to the present invention with the human prorenin.

Figure 2:
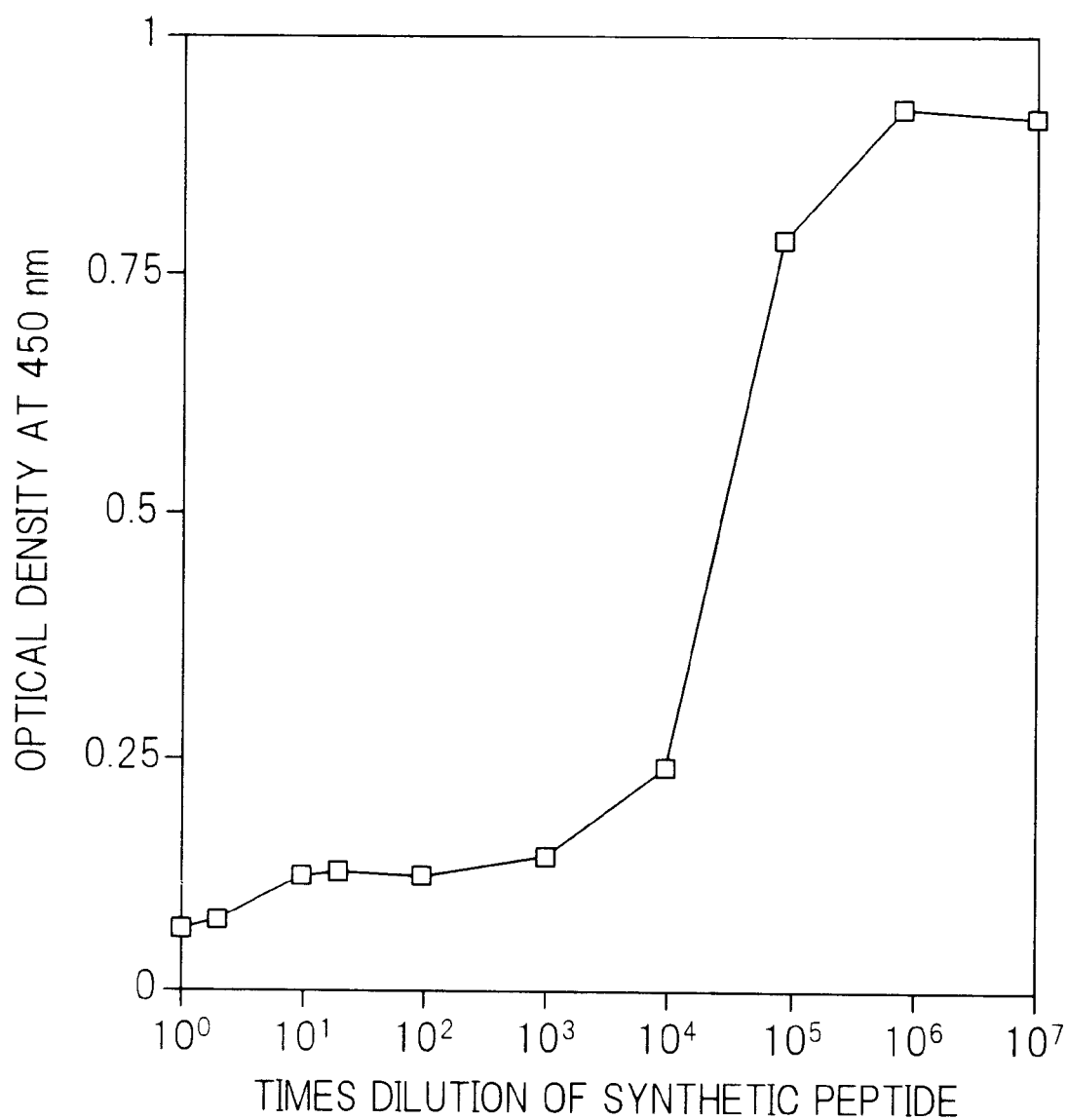
FIG. 2 is a graph showing inhibiting activity of the N-terminated peptide antibody of pf in the reaction of human prorenin with the N-terminated peptide antibody of pf.

FIG. 2 is a graph showing the relationship between the concentration of peptide, when the human prorenin pf N-terminated peptide antibody was admixed with a synthetic pf N-terminated peptide, and the optical density thereof at a wavelength of 450 nm. This graph indicates that the linkage between the human prorenin and the human prorenin pf N-terminated peptide antibody is completely inhibited by the synthetic pf N-terminated peptide or, namely, the linkage exhibits specific activity to the human prorenin.

Figure 3:
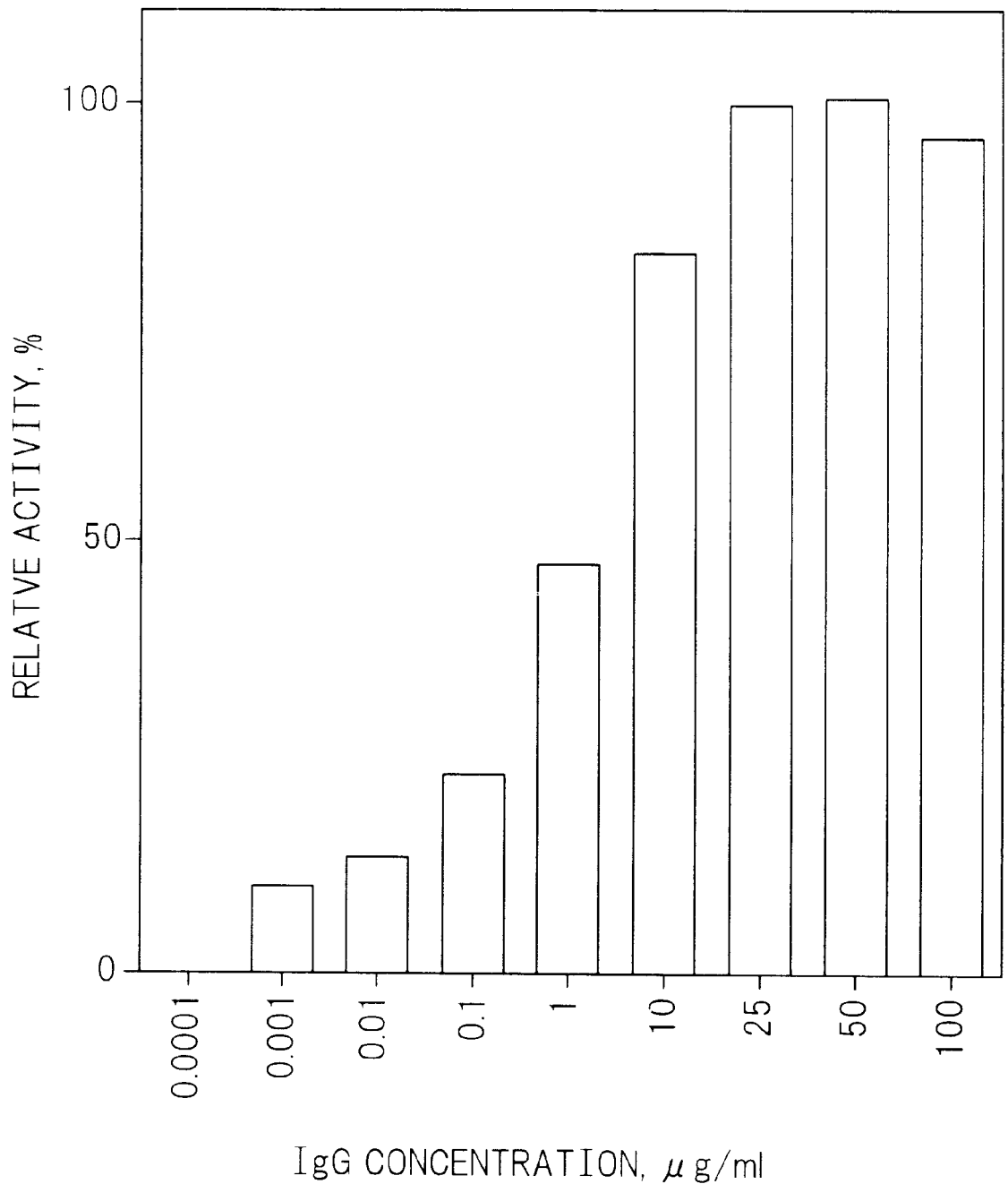
FIG. 3 is a graph showing the dose dependency of the activating capacity of the complex between prorenin and the IgG of the N-terminated peptide antibody of pf.

FIG. 3 is a bar chart showing, for an example of the complexes obtained by the reaction of the human prorenin with the human prorenin pf N-terminated peptide antibody, the renin activity as a function of the concentration given by the relative values taking the renin activity of the human prorenin activated with trypsin as 100%. This chart indicates that the above mentioned complex exhibits the renin activity which depends on the amount of the human prorenin pf N-terminated peptide antibody IgG used there.

Figure 4:
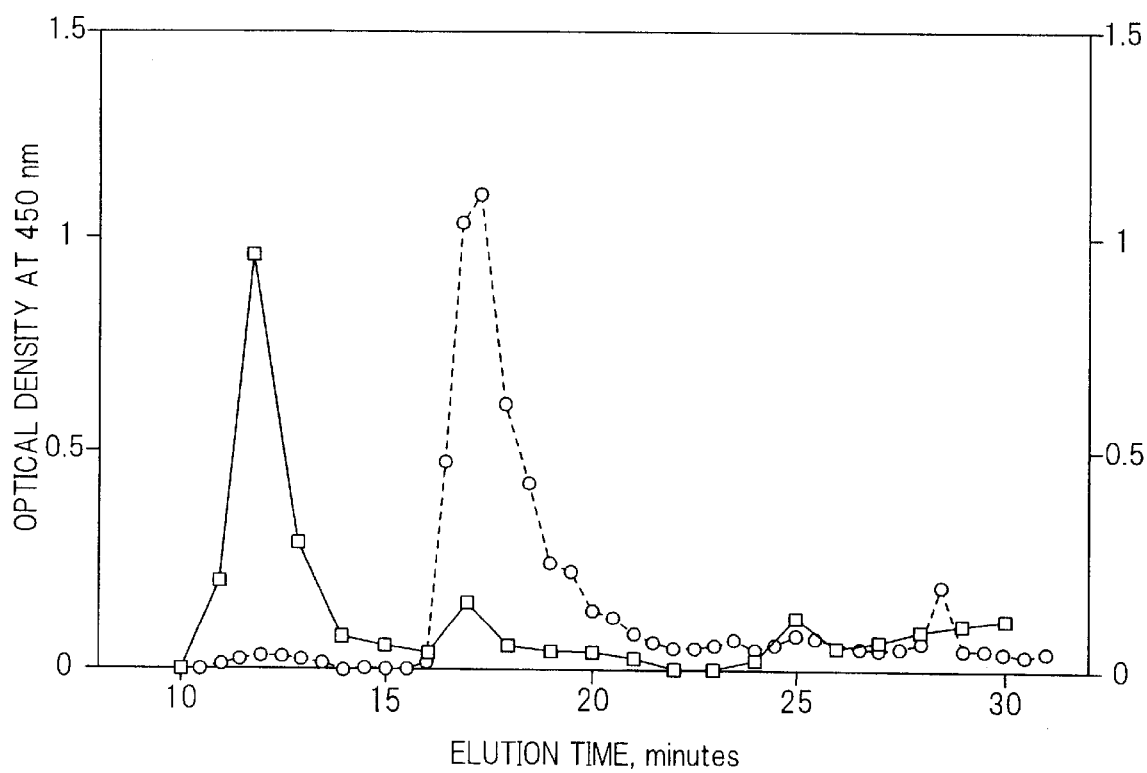
FIG. 4 is a graph showing the relationship between the prorenin-combining capacity of the IgG of the N-terminated peptide antibody of pf and the eluate fractions in the gel filtration chromatography.

Further, the complex of the human prorenin pf N-terminated peptide antibody IgG and the human prorenin is subjected to fractionation by means of the gel filtration high-performance liquid chromatography and each of the fractions is subjected to the assay of the enzymatic activity to give the result shown graphically by the solid line curve in FIG. 4. Similarly, the broken line curve of FIG. 4 shows the result obtained by the enzyme immunoassay of the human prorenin after the gel filtration chromatography by the use of the pf N-terminated peptide antibody and the enzyme-labelled protein A.

Figure 5:
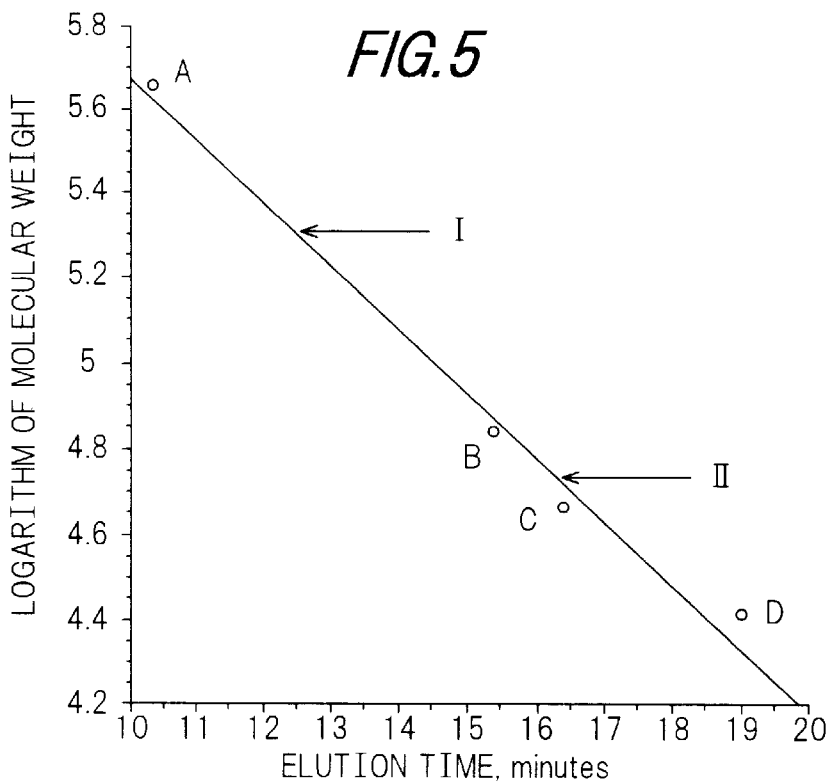
FIG. 5 is a graph for making comparative estimation of the molecular weight of prorenin and the N-terminated peptide antibody of pf.

FIG. 5 is a graph showing the relationship between the molecular weights and the retention times of several known proteins including ferritin having a molecular weight of 450 kD, bovine serum albumin having a molecular weight of 67 kD, ovalbumin having a molecular weight of 45 kD and chymotrypsinogen having a molecular weight of 25 kD indicated by the plots A, B, C and D, respectively, while the retention times of the complex between human prorenin and the pf N-terminated peptide antibody IgG, and the human prorenin are indicated by the arrows I and II, respectively.

As is understood from FIGS. 4 and 5, the enzymatic activity of the complex is mostly found in the fractions with a retention time of 12.0 to 12.5 minutes while the human prorenin is found with a retention time of 16.5 to 17.0 minutes.

The above described facts lead to the conclusion that the enzymatic activity is exhibited by the complex having a molecular weight of 200 to 240 kD between the human prorenin having a molecular weight of 43 kD to 50 kD and the human prorenin pf N-terminated peptide antibody IgG having a molecular weight of 150 kD.

Figure 6:
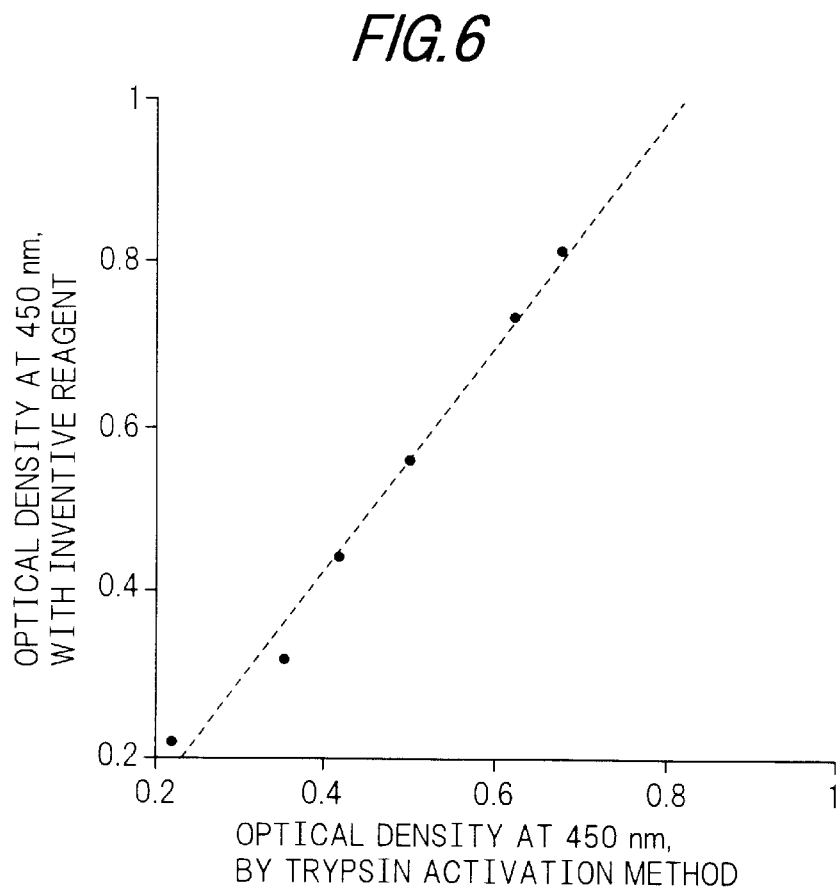
FIG. 6 is a graph showing the correlation between the trypsin activation method and the method by using the assay reagent of the invention.

FIG. 6 is a graph showing the correlation between the titers of human prorenin obtained by the assay using the above mentioned complex and by the trypsin activation method. This graph indicates that a very good correlation with $\gamma=0.986$ is found between the two values.

Using this complex as a prorenin assay reagent, an assay of human prorenin in different concentrations is undertaken to find good linearity of the correlation with the prorenin concentration in the range from 12.5 to 400 ng Ang I/ml.hour.

Figure 8:
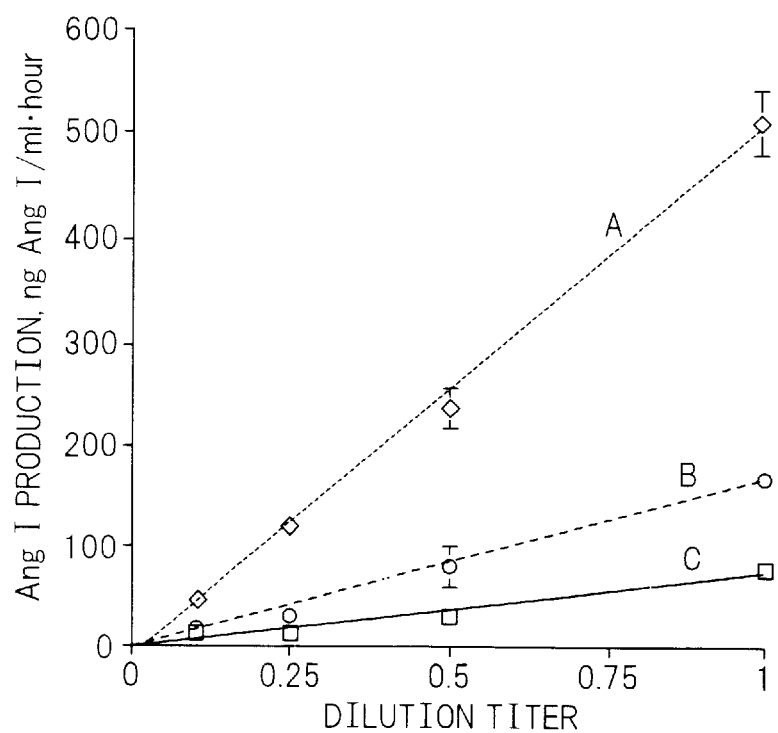
FIG. 8 is a graph showing the enzymatic activity of the inventive assay reagent to three kinds of human prorenins as a function of concentration.

Further, human prorenin serums of high, medium and low concentrations as diluted with human serum for dilution are subjected to the assay of the enzymatic activity by using the same complex as above as the assay reagent to find, as is shown in FIG. 8, good proportionality between the Ang I production and the degree of dilution in each case.

The above described assay tests had good reproducibility with a coefficient of variation of 1.8 to 5.5% for the concurrent reproducibility test with n=7 in different concentrations and 3.8 to 7.5% for the daily reproducibility test with n=5.

The above described results lead to a conclusion that the human prorenin pf N-terminated peptide antibody according to the present invention exhibits high affinity to the human prorenin along with a specific activity on the pf N-terminal and that the complex between this antibody and human prorenin has an enzymatic activity which is in such good correlation with the concentration that the complex is useful as a prorenin assay reagent.

In the following, the present invention is described in more detail by way of Examples, which, however, are not intended to limit the scope of the present invention in any way. Following are the procedures for the preparation of the respective reagents used in the Examples. The titer expression of the prorenin was undertaken by making reference to the Ang I producing activity.

(1) Chromogen solution

The solution was prepared by dissolving tetramethyl benzidine, referred to as TMB hereinafter, in an acetate buffer solution of pH 6.5 in a concentration of 5.5 mM.

(2) Angiotensinogen reagent

Blood was taken from a sheep after 48 hours from bilateral nephrotomy and the blood was immediately subjected to separation of serum which was freeze-dried. A 20 mg portion of the thus obtained dried material was dissolved in 1 liter of a 0.2 M phosphate buffer solution having a pH of 6.5 and containing 10 mmoles of diisopropyl fluorophosphate (DFP) and 10 mmoles of EDTA, referred to as PBS hereinafter, to give the reagent.

(3) Buffer solution for washing

The solution was prepared by dissolving a surface active agent Tween 20 in a concentration of 0.05% by weight in a PBS physiological saline solution.

(4) Human serum for dilution

A commercially available normal human serum supplied by Nippon Biological Materials Center Co. was subjected to an affinity chromatography by using an antibody capable of recognizing both of the completely matured renin and human prorenin to have the completely matured renin and human prorenin adsorbed thereon followed by an inactivation treatment by heating at 56° C. for 30 minutes.

Preparation 1

A master solution of recombinant human prorenin was prepared in the following manner. Thus, according to the method of Murakami, et al. reported in Journal of Hypertensions, volume 4, pages S388–S390 (1986), an expression vector, to which the cDNA of human prorenin derived from a human kidney had been introduced, was built in Chinese hamster ovary cells, referred to as CHO cells hereinafter, and cultured in an Eagle culture medium of the Dulbecco's modified method containing 10% of fetal bovine serum followed by replacement with a serum-free culture medium when the CHO cells had been fully grown to obtain a culture supernatant containing the recombinant human prorenin.

A 5 ml portion of the thus obtained CHO culture supernatant was dialyzed against a PBS physiological saline solution containing 5 mM EDTA followed by adjustment of the concentration of the recombinant human prorenin to 200 $\mu$g Ang I/ml.hour to obtain a recombinant prorenin master solution, which was stored at 4° C.

Preparation 2

Enzyme-labelled Ang I was prepared in the following manner. Thus, 1 ml of a 2.5% glutaraldehyde solution was added dropwise under vigorous agitation into a solution prepared by dissolving 5 mg of horseraddish peroxidase in 500 $\mu$l of 0.2 M PBS. After completion of the dropwise addition of the glutaraldehyde solution, the mixture was agitated for additional 30 minutes at 25° C. and then concentrated into a volume of about 100 $\mu$l by using a membrane filter (Zaltrius Co.) under chilling in an ice bath followed by removal of excess of glutaraldehyde by gel filtration to recover the enzyme fraction.

In the next place, this mixture was further concentrated and admixed with 130 $\mu$l of a solution prepared by dissolving 1 mg of synthetic Ang I peptide in 1 ml of pure water and incubated for 2 hours at 30° C. Thereafter, the reaction was terminated by the addition of 100 $\mu$l of a 0.2 M aqueous solution of lysine and the reaction mixture was again concentrated to have a volume of 100 $\mu$l and removal of the unreacted Ang I by gel filtration to give the desired enzyme-labelled Ang I solution.

The thus obtained enzyme-labelled Ang I solution was admixed with bovine serum albumin, referred to as BSA hereinafter, in a concentration of 0.1% to give an enzyme-labelled Ang I master solution, which was stored at –80° C.

The thus prepared master solution was used after 3000 times dilution with a PBS containing 0.1% of BSA, 0.1 M of sodium chloride and 0.05% of Tween 20.

Preparation 3

An Ang I antibody was prepared in the following manner. Thus, 6.8 mg of a commercially available synthetic Ang I peptide were dissolved in 1 ml of a 0.2 M PBS to give a solution, into which a solution prepared by dissolving 3.4 mg of m-maleimidobenzoyl N-anhydrosuccimide ester, referred to as MBS hereinafter, in 0.5 ml of tetrahydrofuran was added dropwise.

The solution was then kept standing for 30 minutes at 30° C. followed by bubbling of nitrogen gas to evaporate the tetrahydrofuran. The remaining solution was admixed with 5 ml of methylene chloride under agitation followed by centrifugal phase separation to obtain a solution of MBS and Ang I as the aqueous phase.

Separately, a solution prepared by dissolving 10 mg of BSA in 500 μl of a 6 M urea solution containing 0.1 M EDTA was admixed with 20 mg of sodium borohydride and 100 μl of n-butyl alcohol as a defoaming agent and kept standing for 30 minutes followed by the addition of 1 ml of 0.2 M PBS and 0.4 ml of acetone to give a reduced BSA.

The solution of Ang I and MBS and the reduced BSA prepared above were mixed together and incubated for 2 hours at 37° C. to effect the reaction followed by dialysis with PBS to remove the unreacted Ang I.

An immunizing treatment was undertaken with the thus obtained reaction product as the immunoantibody to give an Ang I antiserum.

Preparation 4

An Ang I antibody plate was prepared in the following manner. Thus, the Ang I antiserum obtained in Preparation 3 was diluted 5000 times with a 0.05 M carbonate buffer solution having a pH of 9.6 and a 100 μl portion of the thus diluted solution was added to each well of a 96-well microplate for immunoassay (Maxisorp, a product by Nunc Co.) which was kept standing for 16 to 24 hours at 4° C. Thereafter, the diluted solution in the wells was discarded and replaced with 200 μl per well of a PBS physiological saline solution containing 1% of casein followed by standing as such for at least 16 hours at 4° C. to effect immobilization of the Ang I antibody. The thus prepared plate was stored at 4° C.

EXAMPLE 1

A solution prepared by dissolving 16 mg of keyhole lympet hemocyanin in 1 ml of 0.1 M PBS having a pH of 7.2 was admixed with 100 μl of a dimethylformamide solution of N-(γ-maleimidobutyroxy) succimide in a concentration of 15 mg/ml and kept standing for 3 hours at room temperature. After completion of the reaction, the reaction mixture was freed from the unreacted N-(γ-maleimidobutyroxy) succimide by passing the mixture through a column of Sephadex G-25. Thereafter, elution of the reaction product was conducted with a 0.1 M PBS having a pH of 6.0 and the eluate was admixed with 10 mg of a synthetic peptide consisting of the first to fifteenth amino acid residues at the pf N-terminal of the prorenin freed from the protective groups and kept standing for 3 hours at room temperature to give a complex of prorenin and the pf N-terminated synthetic peptide hemocyanin as an immunoantibody. This solution was stored at −80° C. until use for immunization of animals.

The thus prepared immune antibody was diluted with a physiological saline solution to have a protein concentration of 1 mg/ml and further admixed with equal volume of the complete Freund adjuvant. The whole volume of the thus prepared solution was subcutaneously injected to several points of a New Zealand white rabbit of about 2.5 kg body weight. Immunization of the rabbit was conducted by 7 times of injections at 2 weeks intervals thereafter each time with the immune antibody in a half volume of the volume used in the first injection. After the final immunization, whole blood gathering was conducted from the rabbit and an antiserum was prepared from the blood.

The thus prepared antiserum was dialyzed against a 0.1 M PBS having a pH of 7.0 followed by concentration and then addition of a one-hundredth volume of a solution prepared by dissolving 100 g of sodium azide $NaN_3$ in 1 liter of a physiological saline solution for storage at 4° C.

A 1 ml portion of the above obtained antiserum solution was subjected to a salting-out treatment with sodium sulfate and the solid as precipitated was dissolved in a 17.5 mM PBS having a pH of 6.3. The solution was dialyzed overnight against the same PBS and then passed through a column of DEAE Sepharose equilibrated with the same PBS at a flow rate of 0.3 to 0.5 ml/minute to collect the fraction having light absorption at a wavelength of 280 nm. The solution of this fraction was dialyzed against a 0.1 M PBS having a pH of 7.0 and then concentrated using Centricon-30 (manufactured by Amicon Co.) followed by addition of a one-hundredth volume of the above mentioned sodium azide solution in a concentration of 100 g/liter for storage at 4° C.

The content of protein in the thus obtained pf N-terminated peptide antibody IgG was 2.6 mg/ml as calculated from the optical density at a wavelength of 280 nm assuming a molecular weight of 150,000 for the IgG.

Next, an assay was undertaken in the following manner for the combining activity of the thus obtained pf N-terminated peptide antibody IgG with the human prorenin.

Thus, the recombinant human prorenin master solution in a concentration of 200 μg Ang I/ml.hour prepared in Preparation 1 described above was diluted with a 0.05 M carbonate buffer solution having a pH of 9.6 to have a concentration of 1 μg Ang I/ml.hour and the thus diluted solution was added to each well of a 96-well microplate for immunoassay (Polysorp, a product by Nunc Co.) which was kept standing for at least 16 hours at 4° C. Thereafter, the diluted solution in the wells was discarded and replaced with 200 μl per well of a PBS physiological saline solution having a pH of 7.4 containing 1% of casein followed by standing for at least 16 hours at 4° C. to give a prorenin-immobilized microplate which was stored at 4° C.

Next, the above mentioned pf N-terminated peptide antibody IgG was diluted with a PBS physiological saline solution having a pH of 7.2 and containing 0.1% of BSA and 0.05% of Tween 20 in varied degrees of dilution from 10 times to $10^9$ times. A 100 μl portion of each of the diluted solutions was added to a well of a prorenin-immobilized microplate and kept standing for 2 hours at room temperature to effect the reaction followed by the addition of 100 μl of a solution prepared by 4000 times dilution of peroxidase-labelled protein A (a product by Zymed Laboratories Inc.) containing 0.1% of BSA, 0.1 M of sodium chloride and 0.05% of Tween 20 and standing for 2 hours at room temperature to effect the reaction. After completion of the reaction, the above mentioned solution was discarded from the wells which were repeatedly washed 5 times with 300 μl of the buffer solution for washing.

Thereafter, a 150 μl portion of the chromogen solution was added to each of the wells of the microplate and, after incubation for 5 minutes at 37° C., a 50 μl portion of a 0.03% hydrogen peroxide solution was added to each well followed by incubation for 30 minutes at 37° C.

Finally, the reaction was terminated by the addition of 100 μl of 2 M sulfuric acid and the microplate was subjected to the measurement of the optical density at a wavelength of 450 nm by using a microplate reader (manufactured by Molecular Device Co.) to give the results shown by the graph in FIG. 1. As is clear from this graph, strong affinity to human prorenin was exhibited by the pf N-terminated peptide antibody IgG.

Next, the specificity of the pf N-terminated peptide antibody IgG was investigated by conducting the following inhibition test.

Thus, 1 mg of the above mentioned pf N-terminated synthetic peptide used in the preparation of the antibody was dissolved in 1 ml of a PBS physiological saline solution containing BSA and Tween 20 and the solution was diluted with the same PBS physiological saline solution in different degrees of dilution from 10 times to $10^7$ times to prepare a series of diluted solutions. A 500 µl portion taken from each of the thus diluted solutions was admixed with 10 µl of the pf N-terminated peptide antibody IgG and a 100 µl portion of the solution was added to a well of the prorenin-immobilized microplate which was kept standing for 2 hours at room temperature.

After completion of the reaction, the microplate was repeatedly washed five times with 300 µl of the buffer solution for washing and a 100 µl portion of the peroxidase-labelled protein A solution was added to the well for the measurement of the optical density at a wavelength of 450 nm in the same manner as in the assay of the antibody titer to give the results shown by the graph of FIG. 2. As is understood from this graph, the antigen-antibody reaction between the pf N-terminated peptide antibody and the human prorenin was completely inhibited by the pf N-terminated synthetic peptide as the antigen or, in other words, the pf N-terminated peptide antibody has antigen specificity.

EXAMPLE 2

The CHO culture supernatant obtained in Preparation 1 was diluted by 10 times with a PBS physiological saline solution having a pH of 7.0 and containing 1% of BSA and a 200 µl portion of the thus diluted solution was admixed with 40 µl of an antiserum solution obtained by diluting the pf N-terminated peptide antiserum with a PBS physiological saline solution having a pH of 7.6 and containing 0.1% of BSA in varied degrees of dilution of 10 times to $10^6$ times and kept standing for 16 hours at 4° C.

Thereafter, a 50 µl portion of each of the above obtained reaction mixtures was admixed with 150 µl of the angiotensinogen reagent and incubated for 30 minutes at 37° C.

Next, a 100 µl portion of the above obtained reaction mixture was taken portionwise on the Ang I antibody-immobilized microplate obtained in Preparation 4, which was added with 100 µl of the enzyme-labelled Ang I obtained in Preparation 2 and kept standing for 2 hours at 4° C. After completion of the reaction, the microplate was repeatedly washed three times with 300 µl of the buffer solution for washing and added with 150 µl of the chromogen solution followed by incubation for 5 minutes at 37° C. and further a 50 µl portion of a 0.03% hydrogen peroxide solution was added followed by incubation for 30 minutes at 37° C. to effect the reaction and color development.

Finally, the reaction was terminated by the addition of 100 µl of 2% sulfuric acid and measurement of the optical density at a wavelength of 450 nm was undertaken by using a microplate reader.

Separately, a 200 µl portion of the CHO culture supernatant obtained in Preparation 1 was admixed with 5 µl of a solution prepared by dissolving 1 mg of a trypsin originating in a bovine pancreas (a product by Sigma Co.) in 1 ml of 1 mM hydrochloric acid and kept standing for 10 minutes at 25° C. and the enzymatic reaction of trypsin was terminated by the addition of 5 µl of a solution prepared by dissolving 2 mg of a soybean trypsin inhibitor (a product by Sigma Co.) in 1 ml of a 0.2 M PBS having a pH of 7.4 so as to convert the human prorenin to a completely matured prorenin.

Next, a 100 µl portion of the above obtained reaction mixture was added to the wells of an Ang I antibody-immobilized microplate to conduct the Ang I assay in the above described manner. The results thus obtained are shown by the bar chart in FIG. 3 as the relative activation by the pf N-terminated peptide antibody taking the value of the activation, i.e. amount of Ang I production, by the trypsin of human prorenin as 100%. As is understood from this graph, the complex of the pf N-terminated peptide antibody IgG and human prorenin exhibits dose dependency in the activating capacity.

EXAMPLE 3

A 2 µl portion of a diluted recombinant human prorenin solution in a concentration of 800 ng Ang I/ml.hour was added to 200 µl of the pf N-terminated peptide antibody IgG obtained in Preparation 1 with further addition of a PBS physiological saline solution containing 5 mM of EDTA to make up an overall volume of 500 µl followed by standing for 24 hours at 4° C. to form a complex of the human prorenin and pf N-terminated peptide antibody IgG.

Next, a 100 µl portion of this reaction mixture was applied into a gel-filtration high-performance liquid chromatographic column (Model TSK-GEL-G3000SXL, manufactured by Toso Co.) and elution was performed by using a PBS physiological saline solution containing 5 mM of EDTA at a flow rate of 0.6 ml/minute to collect the eluate solution in fractions of each 0.3 ml volume.

A 50 µl portion taken from each of the fractions was admixed with 50 µl of the angiotensinogen reagent as the renin substrate and incubated for 15 minutes at 37° C. to produce Ang I and then the solution was immediately transferred onto ice and admixed with 150 µl of a PBS containing 0.1% of BSA, 0.1 M of sodium chloride and 0.05% of Tween 20 to make up an overall volume of 250 µl.

Next, a 100 µl portion of this reaction mixture was added to each of the wells of an Ang I antibody-immobilized plate and a 100 µl portion of the enzyme-labelled Ang I solution obtained in Preparation 2 was added thereto followed by standing for 2 hours at 4° C. to effect the reaction. Thereafter, the plate was repeatedly washed three times with 300 µl of the buffer solution for washing.

In the next place, the reaction product was admixed with 150 µl of the chromogen solution and kept standing for 5 minutes at 25° C. followed by the addition of 50 µl of a 0.03% hydrogen peroxide solution for 30 minutes at 25° C.

Finally, the reaction was terminated by the addition of 100 µl of 2 M sulfuric acid and the optical density at a wavelength of 450 nm was measured by using a microplate reader to give the results shown by the solid line curve in FIG. 4. As is understood from this graph, the renin activity, i.e. renin producing activity, was mostly found in the fractions with a retention time of 12.0 to 12.5 minutes.

For comparison, a 100 µl portion of the same diluted solution of recombinant human prorenin solution as used above was subjected to the gel-filtration high-performance liquid chromatography under the same conditions as above and a 100 µl portion taken from each of the eluate fractions was treated in the same manner as in the complex forming test of the pf N-terminated peptide antibody IgG and admixed with the peroxidase-labelled protein A, chromogen solution and 0.03% hydrogen peroxide solution followed by the measurement of the optical density at a wavelength of 450 nm by using a microplate reader to give the results shown by the broken line curve in FIG. 4. As is understood from this graph, the prorenin by the immunoassay method was exhibited almost exclusively by the fractions with a retention time of 16.5 to 17.0 minutes.

With an object to investigate the relationship between the retention time and the molecular weight, a molecular weight marker (a product by Server Co.) was subjected to the gel filtration under the same conditions as above to obtain the results shown in FIG. 5 according to which the prorenin had a molecular weight of about 43 kD to 50 kD somewhat larger than the molecular weight 45 kD of ovalbumin and the complex of prorenin and pf N-terminated peptide antibody IgG had a molecular weight of 200 kD to 240 kD.

A conclusion derived from the above given results is that an immunocomplex exhibiting enzymatic activity or renin activity was formed by the antigen-antibody reaction of prorenin and pf N-terminated peptide antibody and that Ang I was produced by the decomposition of angiotensinogen as the renin substrate.

EXAMPLE 4

A series of diluted solutions were prepared by diluting a prorenin solution of 200 ng Ang I/ml.hour in equivolume dilutions with the human serum for dilution and two sets of samples were prepared by taking a 100 μl portion from each of the diluted solutions.

In the next place, the sample solutions of a first set were subjected to the determination of the Ang I production by the known trypsin activation method and the sample solutions of the second set were subjected to the determination of the Ang I production by using the complex between human prorenin and the pf N-terminated peptide antibody obtained in Example 3.

FIG. 6 is a correlation graph between two sets of values obtained in this way, which indicates good correlation therebetween with a correlation coefficient of $\gamma^2=0.972$.

Figure 7:
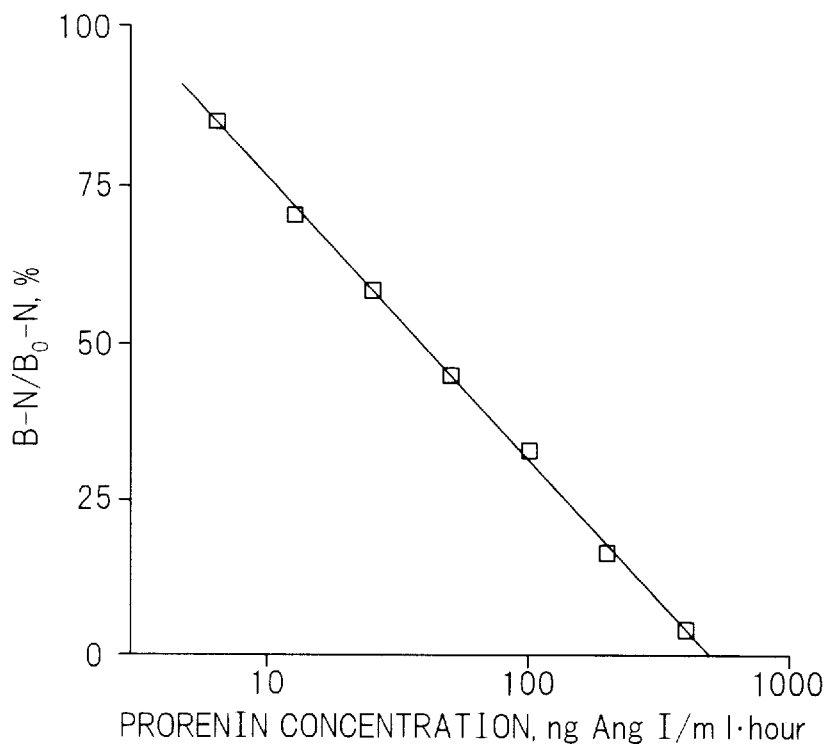
FIG. 7 is a graph showing the relationship between the prorenin concentration and the amount of Ang I production.

In the next place, a series of diluted solutions were prepared by diluting a prorenin solution of 400 ng Ang I/ml.hour in equivolume dilutions with the human serum for dilution and a set of samples were prepared by taking a 100 μl portion from each of the diluted solutions. These samples were subjected to the measurement of the amount of Ang I production by using the above mentioned complex to give the results shown in FIG. 7 which is a graph for the relationship between the prorenin concentration and amount of Ang I production. As is clear from this graph, good linearity is found in the range of the prorenin concentration from 12.5 to 400 ng Ang I/ml.hour.

Further, three series (A), (B) and (C) of diluted human prorenin solutions were prepared by equivolume dilutions of high-, medium- and low-concentration starting solutions of a concentration of 503.2, 160.4 and 70.6 ng Ang I/ml.hour, respectively, with the human serum for dilution and three sets of samples were prepared by taking a 100 μl portion from each of the diluted solutions belonging to the respective series, of which the enzymatic activity was measured by using the above mentioned complex to give the results shown in FIG. 8. As is clear from this figure, a straight line passing through the origin was obtained for the diluted solutions belonging to each of the series.

APPLICATION EXAMPLE

The complex of human prorenin and pf N-terminated peptide antibody obtained in Example 3 was used for the determination of the prorenin titer in the serum samples taken from four healthy adult males of 20 to 40 years old in the manner as in Example 4.

For comparison, the same serum samples were subjected to the determination of the prorenin titer by the conventional trypsin activation method.

The results obtained in these tests are shown in the unit of ng Ang I/ml.hour in the table below for each of the four persons tested.

TABLE

| | Prorenin titer in serum, ng Ang I/ml · hour | |
|---|---|---|
| Case No. | with inventive assay reagent | by trypsin activation |
| 1 | 20.5 | 31.5 |
| 2 | 28.8 | 24.2 |
| 3 | 21.1 | 25.9 |
| 4 | 32.2 | 13.8 |

What is claimed is:

1. An isolated and purified antibody to human prorenin profragment N-terminated peptide, said antibody activating prorenin by specifically recognizing a peptide consisting of 15 amino acid residues from the first leucine residue to the 15th arginine residue in the N-terminated peptide of the human prorenin profragment.

2. A renin-active substance consisting of a complex of the antibody of claim 1 and a human prorenin.

3. A method for the assay of human prorenin in blood which comprises the steps of:

a) reacting human prorenin in blood with an antibody to a human prorenin profragment N-terminated peptide, said antibody activating prorenin by specifically recognizing a peptide consisting of 15 amino acid residues from the first leucine residue to the 15th arginine residue in the N-terminated peptide of the human prorenin fragment, to form a complex which is a renin active substance;

b) adding angiotensinogen as a renin substrate to the renin-active substance to form angiotensin I; and c) determining the angiotensin I.

* * * * *